(12) United States Patent
Line et al.

(10) Patent No.: US 6,368,847 B1
(45) Date of Patent: Apr. 9, 2002

(54) SELECTIVE MEDIA FOR RECOVERY AND ENUMERATION OF CAMPYLOBACTERS

(75) Inventors: John Eric Line, Watkinsville; Johnna Kennedy Garrish, Hull; Kirsten Elizabeth Glassmoyer Pearson, Athens, all of GA (US)

(73) Assignee: The United States of America, as represented by the Secretary of Agriculture, Washington, DC (US)

(*) Notice: Subject to any disclaimer, the term of this patent is extended or adjusted under 35 U.S.C. 154(b) by 0 days.

(21) Appl. No.: 09/583,529

(22) Filed: Jun. 1, 2000

Related U.S. Application Data

(60) Provisional application No. 60/137,782, filed on Jun. 3, 1999.

(51) Int. Cl.⁷ .................................................. C12N 1/20
(52) U.S. Cl. ................................ 435/253.6; 435/252.1; 435/34; 435/244
(58) Field of Search ........................... 435/253.6, 252.1, 435/34, 244

(56) References Cited

U.S. PATENT DOCUMENTS

| | | |
|---|---|---|
| 5,302,388 A | 4/1994 | Doyle et al. |
| 5,891,709 A | 4/1999 | Stern et al. |

FOREIGN PATENT DOCUMENTS

| | | | |
|---|---|---|---|
| EP | 0757888 | * | 2/1997 |

OTHER PUBLICATIONS

Atlas, R. "Handbook of Microbiological Medai", CRC, 1994, pp. 180, 181, 231, 365.*
N. Stern, *Journal of Food Science*, vol. 46, pp. 660–663, 1981.
Christopher et al., *Journal of Food Protection*, vol. 45(3), pp. 260–262, 1982.
A. Castillo–Ayala, *Journal of Food Protection*, vol. 55(5), pp. 333–336, 1992.
Stern et al., *Journal of Food Protection*, vol. 55(7), pp. 514–517, 1992.
Stern et al., *Journal of Food Protection*, vol. 48(7), pp. 606–610, 1985.
Rothenberg et al., *Applied and Environmental Microbiology*, vol. 48(1), pp. 78–80, 1984.
Doyle et al., *Applied and Environmental Microbiology*, vol. 43(6), pp. 1343–1353, 1982.
Bolton et al., *Journal of Applied Bacteriology*, vol. 54, pp. 115–125, 1983.
Bolton et al., *Journal of Clinical Pathology*, vol. 37, pp. 677–681, 1984.
Luechtefeld et al., *Journal of Clinical Microbiology*, vol. 15(1), pp. 137–140, 1982.
M. Hanninen, *Acta vet. Scand.*, vol. 23, pp. 88–98, 1982.
R. Smibert, "Campylocter", In: Bergey's Manual of Systematic Bacteriology, Krieg and Holt (eds.), Williams and Wilkins, Baltimore, MD, vol. 1, pp. 111–115, 1984.
Park et al., *Abstr. Assoc. of Anal. Chem., Annu. Meet.*, vol. 19, p. 3, 1982.

* cited by examiner

*Primary Examiner*—Irene Marx
(74) *Attorney, Agent, or Firm*—M. Howard Silverstein; John D. Fado; Gail E. Poulos

(57) ABSTRACT

A composition for recovery and enumeration of Campylobacter species that includes a selective Campylobacter medium plus an indicator, 2,3,5-triphenyltetrazolium chloride. Improved selective media including the indicator, contains a nutrient medium with an energy source, agar, a reducing agent, and selective agents. The selective agents are a mixture of agents selected from cycloheximide, cefoperazone, vancomycin, trimethoprim, polymyxin B; rifampicin, amphotericin, cefoperazone, vancomycin, trimethoprim, and nystatin. The salts of these agents are also useful.

9 Claims, No Drawings

SELECTIVE MEDIA FOR RECOVERY AND ENUMERATION OF CAMPYLOBACTERS

This invention claims priority of U.S. Provisional Patent Application No. 60/137,782 filed on Jun. 3, 1999.

BACKGROUND OF THE INVENTION

1. Field of the Invention

This invention relates to media containing an indicator, 2,3,5-triphenyltetrazolium chloride, and a selective agent composition; and methods for the recovery and enumeration of Campylobacter species.

2. Description of the Related Art

Campylobacter species have been recognized as important causative agents of foodborne illness. There is a strong association of foods of animal origin in the transmission of disease to humans. Poultry is one such food with high carriage rates of Campylobacter contamination. *Campylobacter jejuni, C. coli* and *C. lari* are known to cause an estimated 2.2 million cases of foodborne gastroenteritis per year in the United States alone (Tauxe et al., American J. Public Health, Volume 77, 1219–1221, 1987). The vast majority of these cases are associated with the consumption of improperly prepared or handled foods. Although the origin of this disease in humans is primarily linked to poultry, the food microbiology and poultry communities have been slow in directing substantive attention toward the organism. This has been due, in part, to the unique physiological requirements of these organisms, impairing their culture and identification from foods and clinical specimens.

A variety of enrichment and culture media have been proposed for the isolation of Campylobacter species (Park et al., Campylobacter, In: Compendium of Methods for the Microbiological Examination of Foods, second ed., M. L. Speck (ed.), Am. Pub. Hlth. Assoc., Wash., D.C., 386–404, 1984—the contents of which are herein incorporated by reference). Because Campylobacter can be overgrown by other organisms present in sources, the use of selective media, incorporating antibiotics and/or antimicrobial agents, is essential for their isolation. Ideally, any culture medium selected should also be differential, allowing the characterization of the Campylobacter by distinctive colonial appearances in culture.

Rapid and sensitive methods for recovering Campylobacter would be useful for both epidemiological work and routine examination of food sources. The main drawback associated with numerous available procedures is the length of time needed for enrichment. Enrichment culture incubation ranges from 16 to 48 hours before plating on selective media, which then requires an additional 24 to 48 hours for isolation. This 3 to 4 day procedure is difficult to reconcile with rapid marketing strategies while maintaining interest in the public health.

The unique physiological requirements of Campylobacter species provide difficulties in culturing the microorganism. *C. jejuni* require special microaerobic atmospheres for growth (Kiggin et al, J. Bacteriology, Volume 72, 397–400, 1956), and its translucent colonies are frequently difficult to identify on dark, opaque Campylobacter agars.

Several agar media have gained prominence for the isolation of Campylobacter. Campy-Brucella Agar Plate (Campy-BAP), has been widely used and cited in the Compendium of Methods for Microbiological Examination of Foods (2nd Ed., American Public Health Association, Wash., D.C., M. L. Speck, ed., 386–404, 1984). Campy-BAP agar contains Brucella agar, lysed horse blood, vancomycin, polymyxin B, trimethoprim lactate, amphotericin B and cephalothin. Food samples assayed with Campy-BAP medium often yield large numbers of breakthrough flora. Butler developed a selective medium for *C. jejuni* containing a nutrient agar base, blood, and five selective agents, cycloheximide, cefazolin, bacitracin, colistin sulfate and novobiocin as described by Smibert (Campylobacter, In: Bergey's Manual of Systematic Bacteriology, Krieg and Holt (eds.), Williams and Wilkins, Baltimore, Md., Volume 1, 111–115, 1984; the contents of which are herein incorporated by reference). Another agar, Campy-Cefex, allows for selective and differential culture of *C. jejuni* (Stern et al., Journal of Food Protection, Volume 55 (7), 514–517, Jul. 1992; U.S. Pat. No. 5,891,709, Apr. 6, 1999). Campy-Cefex agar contains Brucella agar, 0.05% ferrous sulfate, 0.02% sodium bisulfite, 0.05% sodium pyruvate, 33 mg/L sodium cefoperazone, 200 mg/L sodium cycloheximide, and 5% lysed horse blood. CCDA agar contains Nutrient broth No. 2, Bacteriological charcoal, casein hydrosylate, sodium desoxycholate, ferrous sulfate, sodium pyruvate, agar, yeast extract, sodium cefoperazone, and sodium cycloheximide. CCDA medium, also widely used and cited in Compendium of Methods for Microbiological Examination of Foods, (supra), was developed to replace the blood component which is specified in many Campylobacter recovery media, with charcoal. It uses cefoperazone as the selective antimicrobial agent acting in concert with a 42° C. incubation temperature and microaerobic atmosphere to limit the proliferation of non-Campylobacter organisms. The 42° C. incubation temperature greatly reduces the need for anti-gram-positive antimicrobials. The ferrous sulfate component of the medium has been used to enhance the growth and aerotolerance of Campylobacter spp. The main disadvantage of CCDA medium is its dark opacity, making it difficult to differentiate between Campylobacter spp. and non-Campylobacter spp. flora. Cefoperazone does not inhibit growth of molds and yeast on CCDA medium which can be associated with poultry samples.

Rothenberg et al (Applied and Environmental Microbiology, Volume 48(1), 78–80, Jul. 1984) disclose an attempt to develop an enrichment broth requiring only 7 hours of incubation and the comparison of their broth with that described by Doyle and Roman (Applied Environmental Microbiology, Volume 43, 1343–1353, 1982) and Park and Stankiewicz (Abstr. Assoc. Of Anal. Chem., Annu. Meet., volume 19, page 3, 1982). The Rothenberg et al. medium was a modification of the Doyle Roman broth and additionally contains 0.2% ferrous sulfate, 0.025% sodium metabisulfite, 0.05% sodium pyruvate, 0.1% sodium lauryl sulfate, and 0.075% agar. The Doyle and Roman broth contains Brucella broth, 7% lysed horse blood, 0.3% sodium succinate, 0.01% cysteine hydrochloride, vancomycin (15 µg/ml), trimethoprim (5 µg/ml), polymyxin B (20 IU/ml), and cycloheximide (50 µg/ml). After a 16 to 18 hour incubation, the medium containing inoculum is plated directly onto Campy-BAP agar plates. The Stankiewicz broth contains vancomycin (20 mg/l), trimethoprim (10 mg/l), polymyxin B (5,000 IU/l for monophasic broth and 7,500 IU/l for diphasic medium), and lysed horse blood (5%, optional) in brucella broth. For the monophasic medium, 50 ml of the enrichment broth is placed in a 250 ml-Erlenmeyer flask. For the diphasic medium, brucella agar base (30 ml) with an overlay of the enrichment broth (50 ml) was made in a 500 ml-Erlenmeyer flask. Two other media are disclosed by Rothenberg. One contains 25 ml Brucella broth supplemented with 0.2% ferrous sulfate, 0.025% sodium metabisulfite, and 0.05% sodium pyruvate. The other, a selective medium, contains blood agar base no. 2 (Oxoid Ltd., London, England), 5% lysed horse blood, 10 μg/ml vancomycin, 2.5 IU/ml polymyxin, 5 μg/ml trimethoprim, and 15 μg/ml cephalothin.

Castillo-Ayala (Journal of Food Protection, Volume 55(5), 333–336, May 1992) disclose enrichment broths for isolation of *Campylobacter jejuni/coli* from freshly deboned market chicken. The first broth, VTP broth, contained 25 ml of double strength Brucella broth, 0.025% of sodium metabisulfate, 0.025% sodium pyruvate, 20 μg/ml vancomycin, 10 μg/ml trimethoprim, 5 IU polymyxin B. The other, BCN, contained 25 ml of double strength Brucella broth, 0.025% sodium metabisulfate, 0.025% sodium pyruvate, 50 IU/ml bacitracin, 20 IU/ml novobiocin, and 10 μg/ml cycloheximide. They concluded that the vancomycin-trimethoprim-polymyxin B mixture was not a suitable agent for use in an enrichment-plating procedure to recover Campylobacter from poultry.

Christopher et al (Journal of Food Protection, Volume 45(3), 260–262, Feb., 1982) disclose a method and media for isolation and enumeration of *Campylobacter fetus* subsp. *jejuni* that included a subculturing step that used Brucella broth containing 0.15% agar, 0.05% sodium pyruvate, 10 mg/liter vancomycin, 5 mg/liter trimethoprim, 2,500 IU/liter polymyxin B sulfate, 2 mg/l amphotericin B, and 15 mg/l cephalothin followed by subsequent streaking on plates of Brucella agar supplemented with 10% defibrinated horse blood and 10 mg/liter vancomycin, 5 mg/liter trimethoprim, 2,500 IU/liter polymyxin B sulfate, 2 mg/liter amphotericin B, and 15 mg/liter cephalothin.

U.S. Pat. No. 5,302,388 (Doyle et al; Apr. 12, 1994) discloses an enrichment broth for *Campylobacter jejuni* containing Brucella broth, 7% lysed horse blood, 0.3% sodium succinate or 0.01% cysteine hydrochloride, 15 μg vancomycin/ml, 5 μg trimethoprim/ml, 20 IU polymyxin B/ml, and 50 μg cycloheximide/ml.

Luechtefeld and Wang (J. Clin. Microbiol., Volume 15(1), 137–140, January 1982) disclose the use of 1 mg or 400 μg of 2,3,5-triphenyltetrazolium chloride (TTC) per ml of a medium containing brucella agar and sheep blood for differentiating *C. fetus* subsp. *jejuni* from *C. fetus* subsp. *intestinalis*. They report that all strains of *C. fetus* subsp. *intestinalis* were sensitive to 400 μg/ml of TTC and all strains of *C. fetus* subsp. *jejuni* were insensitive to 400 μg/ml TTC. The reference also discloses that Veron and Chatelain (Intl. J. Syst. Bacteriol., Volume 23, 122–134, 1973) found that none of the 18 strains of *C. fetus* subsp. *fetus* (*C. fetus* subsp *intestinalis* of Smibert (supra)) grew on blood agar containing 1 mg/ml of TTC in contrast to 9 strains of *Campylobacter coli* and 1 strain of *C. jejuni*.

Hanninen (Acta vet. scand., Volume 23, 88–98, 1982) disclose testing the tolerance of the *C. jejuni/coli* group to 1 mg/liter of TTC. The reference states that most strains in their study tolerated TTC. It further states that according to Skirrow & Benjamin, *C. jejuni* strains are sensitive to TTC and *C. coli* strains tolerated it. The reference further states that there are differences in TTC tolerance between the Campylobacter strains investigated by different authors and that most of the TTC tests made earlier and in their studies have been performed on a blood agar substrate containing TTC. Hanninen concludes that the blood in the substrate may be one reason why so many of the present strains tolerated TTC and the reference also observed that Skirrow & Benjamin did not use a blood-containing medium in their tests. The reference further discloses that the optimum TTC concentration for TTC reduction of *C. fetus* and related vibrios is shown to be 400 μg/ml and notes that TTC has been used in a concentration range of 400 μg/ml to 1 mg/ml.

Existing media for the recovery and enumeration of colonies of Campylobacter species often contain many colonies of contaminating microorganisms and are difficult to enumerate because of the translucent nature of Campylobacter colonies. Therefore, there is a need in the art for media which recover high populations of Campylobacter with fewer contaminating colonies and which are easily enumerated. The present invention, described below, is improved media which provide selectivity for Campylobacter species while increasing the contrast of the colonies with the media to simplify counting procedures and is different from related art media.

SUMMARY OF THE INVENTION

It is therefore an object of the present invention to provide improved media for recovery and enumeration of Campylobacter species.

Another object of the present invention is to provide improved media for the recovery and enumeration of Campylobacter species, the improvement includes an indicator for facilitating accurate enumeration of Campylobacter colonies.

A further object of the present invention is to provide improved media for the recovery and enumeration of Campylobacter species wherein the indicator is 2,3,5 Triphenyltetrazolium chloride (TTC).

A still further object of the present invention is to provide improved media for the recovery and enumeration of Campylobacter species wherein the 2,3,5 Triphenyltetrazolium chloride concentration is about 200 μg/ml or less.

A further object of the present invention is to provide improved media for the recovery and enumeration of Campylobacter species which is a blood-containing or a blood-free media.

A still further object of the present invention is to provide a media which contains a selective agent composition to provide improved selectivity for Campylobacter species.

Further objects and advantages of the present invention will become apparent from the following description.

DETAILED DESCRIPTION OF THE INVENTION

The media of this invention may be used for the isolation and enumeration of Campylobacter species such as, for example, *C. jejuni, C. coli, C. lari*, etc., from a variety of sources. Although the media are particularly valuable for the growth and recovery of this microorganism from samples taken from poultry carcasses, especially chicken, it is understood that the media may also be used for the isolation of Campylobacter from any samples suspected of containing this pathogen. Without being limited thereto, other sources include animal carcasses such as cattle and sheep, food, milk, water, or environmental samples, or clinical sources such as blood or feces. The culture media contemplated for use in this invention may be prepared using techniques conventional in the art. The basal medium components including agar and/or nutrient media with an energy source are mixed, heated to boiling and sterilized by autoclaving. After cooling the sterilized medium to about 50° C.–55° C., blood and filter-sterilized supplements are added with mixing, pH asceptically adjusted to about pH 7.4 with, for example, 10N NaOH, and the medium finally poured into a culture container, such as a petri dish, for example, and cooled to allow the agar to solidify.

In one embodiment of the present invention, the basal medium components selected for use are not critical and may be readily determined by the practitioner skilled in the art, one of the improvements includes the addition of an indicator, 2,3,5-triphenyltetrazolium chloride in amounts which do not significantly inhibit the growth of Campylobacter species. Any nutrient medium and energy source effective to support growth of Campylobacter species may be used. Suitable nutrient media include, for example, but are not limited to Brucella agar (e.g. BBL, Cockeysville, Md.; Difco Laboratories, Detroit, Mich.;) CM 691 (Oxoid, Columbia, Md.), Campylobacter agar base (Difco), Blood agar base No. 2 (Oxoid), Brain-heart infusion agar (BBL;Difco), or Columbia Blood Agar Base. A variety of energy sources may also be employed, and may be incorporated into commercially available nutrient media or added separately. In the preferred embodiments of the present invention, Brucella agar (Acumedia) is the preferred nutrient medium. Suitable energy sources for use in the media are described by Sibert (INL Bergey's Manual; supra, the contents of which are herein incorporated by reference) and include pyruvate, citrate, succinate, cis-aconitate, α-ketoglutarate, fumarate, malate, and oxaloacetate.

For all embodiments of the present invention, the source of blood added to the medium also is not critical. While horse blood is preferred, it is understood that other blood sources may be used, such as for example, sheep blood. For blood-free media, hemin, yeast extract, sodium carbonate and α-ketoglutaric acid are used to replace the blood component.

Selective agents, for use in all embodiments of the present invention, are used to prevent the growth of contaminating microorganisms present in samples to be tested, but which do not inhibit growth of Campylobacter species. The selective agents include any selective agent or combination thereof known to one of ordinary skill in the art. Improved preferred selective agents include vancomycin, trimethoprim, polymyxin B, cycloheximide, rifampicin, nystatin, amphotericin, and cefoperazone, their salts, and mixtures thereof. The combination of these preferred agents provides excellent selectivity for Campylobacter species.

An indicator, for use in all embodiments of the present invention, is included in Campylobacter media to facilitate manual or automated enumeration of Campylobacter colonies. The indicator 2,3,5-triphenyltetrazolium chloride (TTC; Sigma) is used in a concentration range of about 50 µg/ml to about 250 µg/ml. The preferred concentration is about 200 µg/ml.

Other adjuvants, useful in all embodiments of the present invention, may also be incorporated into the media for enhancing growth and/or aerotolerance of Campylobacter. Preferred adjuvants enhancing aerotolerance are described by Smibert (supra) and include but are not limited to sodium pyruvate or pyruvic acid, ferrous sulfate, bovine superoxide dismutase, catalase and reducing agents such as sodium bisulfite or sodium metabisulfite. Particularly preferred for addition to medium are ferrous sulfate, pyruvic acid, and sodium bisulfite. It is understood that the use of blood in the media also enhances aerotolerance because it contains heme, catalase and superoxide dismutase.

The concentration and amount of each of the components of the Campy-TTC blood-containing medium, a particularly preferred embodiment of the present invention, are variable and may be readily determined by the practitioner skilled in the art. The amount of each component of the basal or nutrient media should be effective to promote growth of Campylobacter species, while the amount of the selective agents should be effective to inhibit growth of contaminating (non-Campylobacter) microorganisms without substantially inhibiting growth of Campylobacter species relative to culture medium lacking these selective agents. Without being limited thereto, preferred ranges of the selective agents include about 20–50 mg/liter cefoperazone, about 100–400 mg/liter cycloheximide, about 5–20 milligrams/liter vancomycin, about 2.5–10 milligrams/liter trimethoprim, about 5–20 milligrams/liter polymyxin, about 5–20 milligrams/liter rifampicin, about 10–40 milligrams/liter amphotericin, about 20–80 milligrams/liter nystatin, and about 100–250 mg/liter 2,3,5-Triphenyltetrazolium chloride.

In accordance with a particularly preferred formulation of blood-containing Campy-TTC, ranges of the amount of each component per liter include but are not limited to:

| | |
|---|---|
| Brucella Agar | about 40–50 grams |
| lysed horse serum | about 20–100 ml (about 2–10%) |
| Sodium Cycloheximide | about 100–400 mg |
| Sodium Cefoperazone | about 20–50 mg |
| Ferrous sulfate | about 0.1–1 gram |
| Sodium Bisulfite | about 0.05–5 grams |
| Pyruvic Acid | about 0.1–1 gram |
| Vancomycin | about 5–20 milligrams |
| Trimethoprim | about 2.5–10 milligrams |
| Polymyxin B | about 0.3–0.75 milligrams |
| TTC | about 100–250 milligrams |
| distilled water | about 1000 ml. |

The final pH of the medium should generally be between about 6.5 to about 7.8, pH 7.4 is preferred.

In accordance with another particularly preferred formulation, blood-free Campy-TTC, ranges of the amount of each component per liter include but are not limited to:

| | |
|---|---|
| Brucella Agar | about 40–50 grams |
| lysed Horse Blood | about 20–100 ml (about 2–10%) |
| Rifampicin | about 5–20 mg |
| Amphotericin | about 10–40 mg |
| Sodium Cefoperazone | about 20–50 mg |
| Ferrous sulfate | about 0.1–1 gram |
| Sodium Bisulfite | about 0.05–5 grams |
| Pyruvic Acid | about 0.1–1 gram |
| Vancomycin | about 5–20 milligrams |
| Trimethoprim | about 2.5–10 milligrams |
| Polymyxin B | about 0.3–0.75 milligrams |
| TTC | about 100–250 milligrams |
| distilled water | about 1000 ml. |

The final pH of the medium should generally be between about 6.5 to about 7.8, pH 7.4 is preferred.

In accordance with another particularly preferred formulation, blood-free Campy-TTC, ranges of the amount of each component per liter include but are not limited to:

| | |
|---|---|
| Brucella Agar | about 40–50 grams |
| lysed Horse Blood | about 20–100 ml (2–10%) |
| Rifampicin | about 5–20 mg |
| Nystatin | about 20–80 mg |
| Sodium Cefoperazone | about 20–50 mg |
| Ferrous sulfate | about 0.1–1 gram |
| Sodium Bisulfite | about 0.05–5 grams |

-continued

| | |
|---|---|
| Pyruvic Acid | about 0.1–1 gram |
| Vancomycin | about 5–20 milligrams |
| Trimethoprim | about 2.5–10 milligrams |
| Polymyxin B | about 0.3–0.75 milligrams |
| TTC | about 100–250 milligrams |
| distilled water | about 1000 ml. | final pH of the medium should generally be between about 6.5 to 7.8, pH 7.4 is preferred.

In accordance with another particularly preferred formulation, blood-free Campy-TTC, ranges of the amount of each component per liter include but are not limited to:

| | |
|---|---|
| Brucella Agar | about 40–50 grams |
| Ferrous Sulfate | about 0.1–1 gram |
| Sodium bisulfite | about 0.05–5 grams |
| Pyruvic Acid | about 0.1–1.0 gram |
| α-ketoglutaric acid | about 0.5–2.5 grams |
| Sodium carbonate | about 0.4–0.8 gram |
| Yeast extract | about 2–5 grams |
| Sodium cefoperazone | about 20–50 milligrams |
| Sodium cycloheximide | about 100–400 milligrams |
| Vancomycin | about 5–20 milligrams |
| Trimethoprim | about 2.5–10 milligrams |
| Polymyxin B | about 0.3–0.75 milligrams |
| TTC | about 100–250 milligrams |
| Hemin | about 5025 milligrams |
| distilled water | about 1000 ml. |

The final pH of the medium should generally be between about 6.5 to 7.8, pH 7.4 is preferred. Effective amounts of each ingredient are those amounts which promote growth of Campylobacter species.

In accordance with another particularly preferred formulation, blood-free Campy-TTC, ranges of the amount of each component per liter include but are not limited to:

| | |
|---|---|
| Brucella Agar | about 40–50 grams |
| Ferrous Sulfate | about 0.1–1 gram |
| Sodium bisulfate | about 0.05–5 grams |
| Pyruvic Acid | about 0.1–1.0 gram |
| α-ketoglutaric acid | about 0.5–2.5 grams |
| Sodium carbonate | about 0.4–0.8 gram |
| Yeast extract | about 2–5 grams |
| Sodium cefoperazone | about 20–50 milligrams |
| Rifampicin | about 5–20 mg |
| Amphotericin | about 10–40 mg |
| Vancomycin | about 5–20 milligrams |
| Trimethoprim | about 2.5–10 milligrams |
| Polymyxin B | about 0.3–0.75 milligrams |
| TTC | about 100–250 milligrams |
| Hemin | about 5–25 milligrams |
| distilled water | about 1000 ml. |

The pH of the medium should generally be between about 6.5 to 7.8, pH 7.4 is preferred. Effective amounts of each ingredient are those amounts which promote growth of Campylobacter species.

In accordance with another particularly preferred formulation, blood-free campy-TTC, ranges of the amount of each component per liter include but are not limited to:

| | |
|---|---|
| Brucella agar | about 40–50 grams |
| Ferrous Sulfate | about 0.1–1 gram |
| Sodium bisulfite | about 0.05–5 grams |
| Pyruvic Acid | about 0.1–1.0 gram |
| α-ketoglutaric acid | about 0.5–2.5 grams |
| Sodium carbonate | about 0.4–0.8 gram |
| Yeast extract | about 2–5 grams |
| Sodium cefoperazone | about 20–50 milligrams |
| Rifampicin | about 5–20 mg |
| Nystatin | about 20–80 mg |
| Vancomycin | about 5–20 milligrams |
| Trimethoprim | about 2.5–10 milligrams |
| Polymyxin B | about 0.3–0.75 milligrams |
| TTC | about 100–250 milligrams |
| distilled water | about 1000 ml. |

The final pH of the medium should generally be between about 6.5 to 7.8, pH 7.4 is preferred. Effective amounts of each ingredient are those amounts which promote growth of campylobacter species.

In use, the sample to be analyzed is inoculated onto the culture medium using techniques conventional in the art and is incubated for a sufficient time and under conditions effective to promote growth of Campylobacter species. Suitable conditions may be readily determined by the practitioner skilled in the art and are described by Smibert (supra). Without being limited thereto, preferred conditions include a temperature between about 35° C. to about 44° C., especially about 42° C. to about 43° C., and a low oxygen tension (i.e., microaerobic), especially an oxygen concentration of between about 3–6%. Techniques for generating this reduced atmosphere are well known in the art and are described in, for example, Inoue (U.S. Pat. No. 4,904,597), or Hutchinson and Bolton (J. Clin. Pathol., Volume 36, 1350–1352, 1983), or Park et al. (supra), the contents of each of which are herein incorporated by reference.

Following incubation, generally after about 24–48 hours, the culture may be examined for the presence of colonies indicative of Campylobacter. Colonies of Campylobacter on any of the preferred Campy-TCC media of this invention are deep red to magenta in color. These colonies can be readily discriminated from non-Campylobacter breakthrough flora. Further confirmatory testing of the colonies and speciation can be conducted as described by Park et al (supra) or Smibert (supra). The use of these agars containing 2,3,5-triphenyltetrazolium chloride would be a benefit to technicians in enumerating and confirming Campylobacter colonies. The use of Campy-TTC agars, either blood-containing or blood-free with a preferred selective agent composition, also is a benefit because of the increased selectivity of the agars. Automated counting methods may also be made possible using triphenyltetrazolium chloride containing agars since the darker colonies contrast sufficiently with the agar base to allow detection by electronic means.

The following examples are intended to further illustrate the invention and are not intended to limit the scope of the invention as defined by the claims.

EXAMPLE 1

This example compares Campy-cefex agar and blood-containing Campy-TCC and blood-free Campy-TCC. Campy-TCC agar is prepared as follows: Approximately 43 grams of Brucella agar (Acumedia), approximately 0.5 grams of ferrous sulfate, approximately 0.2 grams of sodium bisulfite, approximately 0.5 gram of pyruvic acid, and about 1000 milliliters of distilled water are mixed in a large Erlenmeyer flask and heated to boiling. This is then autoclaved for about 15 minutes at about 121° C. and about 21 psi pressure. The media is then cooled to about 50° C.

The selective supplements are prepared as follows: In a 100 ml volumetric flask, about 0.1 grams trimethoprim is dissolved in about 20 milliliters of 100% ethanol. Approximately 0.2 grams vancomycin and approximately 0.007 grams polymyxin B are added and the flask filled to 100 ml with deionized water. Some gentle heating may be required to complete dissolution. Filter sterilize using a 0.22 μm filter and dispense into cryovials. Store at about −80° C. and use about 5 ml/liter agar. Approximately 2.0 grams cycloheximide are dissolved in about 10 ml of about 50% methanol and filter sterilized using a 0.22 μm filter. About 0.5 ml/liter of this solution is used. The cycloheximide is prepared fresh for use. Approximately 1 grams cefoperazone is dissolved in about 10 ml of deionized water and filter sterilized using a 0.22 μm filter. This is then dispensed into sterile cryovial tubes and stored at about −80° C. About 0.33 ml/liter is used for 33 mg/liter.

The 2,3,5-triphenyltetrazolium chloride is prepared as about a 20% stock solution in deionized water (about 20 grams/100 ml). Slight heating will be necessary to complete dissolution. This is then filter sterilized with, for example, a 0.2 μm filter or autoclaved for about 15 minutes at about 121° C. and about 21 PSI pressure, and stored at about 4° C. About 1 milliliter is used per liter of media. The solution will crystallize at refrigeration temperatures, but gentle heating will get it back into solution.

The selective supplements, 2,3,5-triphenyltetrazolium salts, and approximately 50 ml. Of lysed horse blood (Lampire Biologicals) are added to the autoclaved media after cooling to about 50° C. to form a complete media. The media is dispensed into petri dishes (100×15 mm, 20 ml/plate). Media should be made about 2 days prior to intended use and held in the dark at room temperature to allow sufficient time for the agar plates to dry. Plates may be made up to about 2 weeks prior to use and held in the dark at about 4–6° C. If plates are held at about 4–6° C., allow 1–2 days at room temperature for drying.

The blood-free media is prepared by mixing approximately 43 grams of Brucella agar, approximately 0.5 grams ferrous sulfate, approximately 0.2 grams of sodium bisulfite, approximately 0.5 grams pyruvic acid, approximately 1.0 grams α-ketoglutaric acid, approximately 0.6 gram sodium carbonate, approximately 3.0 grams yeast extract and about 1000 ml of distilled water. This mixture is heated to boiling and then autoclaved for about 15 minutes at approximately 121° C. and then cooled to 50° C.

Supplements for the blood-free media are prepared as follows: Approximately 0.5 gram of hemin is dissolved in about 10 ml of sodium hydroxide, 1N. Approximately 90 ml of distilled water is added and the solution is autoclaved for about 15 minutes at about 121° C. Approximately 2 ml/liter is added to the cooled media. Selective supplements including vancomycin/trimethoprim, polymyxin B, cycloheximide, and cefoperazone are prepared and used as described above for the blood-containing media. The 2,3,5-triphenyltetrazolium chloride is also prepared and used as described above for the blood-containing media. All supplements are added to the cooled media and the complete media is dispensed into petri dishes as described above for the blood-containing Campy-TTC media.

A mixture of 7 wild type (non-Campylobacter) strains commonly isolated as contaminants on Cefex agar from poultry carcass rinses was prepared from Campy-Cefex plates grown overnight at about 42° C. under microaerobic conditions. Microaerobic conditions means using Campy gas which is about 5% oxygen, about 10% carbon dioxide, and about 85% nitrogen. Individual strains of C. jejuni (4 strains) and C. coli (4 strains) were likewise grown overnight on Cefex agar. The contaminant mixture was diluted and equally divided into 8 portions. Each portion was inoculated with approximately equal populations of a single strain of C. jejuni or C. coli. The resulting mixtures of contaminants and single strains of Campylobacter were plated for recovery and isolation of Campylobacters on Campy-Cefex agar, Campy-TTC, and blood-free Campy-TCC. Plates were incubated upside down in an incubator charged with Campy gas at about 42° C. After about 40–42 hours of incubation, the plates were removed and a differential count of each plate was performed. Campylobacter and non-Campylobacter colonies were enumerated.

Results are shown below in Table 1. Both the Campy-TCC agar and the blood-free Campy-TTC agar recovered higher populations of *Campylobacter jejuni* and *C. coli* than did Campy-Cefex agar. More significantly, no contaminants of those tested were isolated on the Campy-TTC agar or the blood-free Campy-TTC agar, while a mean of about 600 non-Campylobacter contaminant cfu/ml were found to grow on Campy-Cefex agar. The Campy-TTC and the blood-free Campy-TTC agars contained different selective antibiotics as well as low levels of triphenyltetrazolium chloride as an indicator. This indicator gave a deep red to magenta color to the otherwise translucent Campylobacter colonies making observation easier.

TABLE 1

Mean Campylobacter and contaminant recovery by Campylobacter strain and agar type

| Campylobacter Strain | Campy-Cefex agar | | Campy-TTC agar | | Blook-free Campy-TTC agar | |
|---|---|---|---|---|---|---|
| | Mean Campy cfu/ml | Mean contam. cfu/ml | Mean Campy cfu/ml | Mean contam. cfu/ml | Mean campy cfu/ml | Mean contam. cfu/ml |
| C. jejuni — #1 | 8100 | 700 | 7400 | 0 | 6900 | 0 |
| C. jejuni — #2 | 2400 | 500 | 5400 | 0 | 5800 | 0 |
| C. jejuni — #3 | 4400 | 300 | 5700 | 0 | 5300 | 0 |
| C. jejuni — #5 | 2000 | 600 | 4900 | 0 | 3400 | 0 |
| C. coli — #8 | 6900 | 500 | 8800 | 0 | 7600 | 0 |
| C. coli — #9 | 5600 | 600 | 4000 | 0 | 4000 | 0 |
| C. coli — #10 | 900 | 400 | 1400 | 0 | 1200 | 0 |
| C. coli — #11 | 2300 | 1200 | 1500 | 0 | 2100 | 0 |
| Mean C. jejuni (4 strains) | 4200 | 525 | 5900 | 0 | 5400 | 0 |
| Mean C. coli (4 strains) | 3900 | 575 | 3900 | 0 | 3700 | 0 |
| Mean C. jejuni/ coli (8 strains) | 4100 | 600 | 4900 | 0 | 4600 | 0 |

EXAMPLE 2

In this example, recovery of Campylobacter from naturally occurring contaminated poultry carcass rinses is compared using Campy-cefex and the blood-containing Campy-TTC agars. Buffered peptone water (BPW) for rinsing and dilution blanks were prepared and kept cold at about 4° C. Agar plates were made as described in Example 1 approximately 72 hours prior to use and allowed to sit in the dark at room temperature.

Freshly processed broiler carcasses, (20, post-chill, post drip) were procured from a commercial processing plant early in the morning of the day of analysis. The carcasses were individually placed in large plastic bags (Cryovac) and transported on ice. BPW (about 4° C.) was aseptically added (about 400 ml) to each of the samples. The carcasses with BPW were agitated for about 2 minutes using a carcass shaking machine to standardize the rinse procedure. After the samples were removed from the carcass shaking machine, about a 200 ml. portion of the rinse from each carcass was carefully poured off into individual sterile sample containers. Containers were labeled with the sample number (1–20).

Approximately 0.25 ml. samples from each original carcass rinse were transferred to each of 4 properly dried Campy-Cefex agar plates and spread thoroughly with sterile "hockey sticks". The plating procedure was repeated using 4 blood-containing Campy-TTC agar plates. All plates were incubated upside down an incubator charged with Campy gas for about 36–48 hours at about 42° C.

Directly inoculated agar plates were removed from the incubators after about 36–48 hours. Plates were inspected for growth of Campylobacter. Typical Campylobacter colonies were enumerated and confirmed using microscopic wet mount and latex agglutination for confirmation as necessary. Typical colonies (about 3–4) were picked from plates and pooled in about 25 microliters of about 0.85% saline. This slurry was used to prepare microscopic wet mounts and to confirm using the latex agglutination assay (Integrated Diagnostics, Inc., Baltimore, Md.). Non-Campylobacter contaminating colonies were also enumerated on each agar type.

Campylobacter populations enumerated from the directly plated (about 0.25 ml.) samples were very low, generally about 0–13 cfu/plate. Campy-Cefex plates incubated in the Campy gas charged incubator showed about 95% of the samples to be positive for Campylobacter, while Campy-TTC agar plated incubated under similar conditions showed 100% of the samples to be positive. The mean total colony count per milliliter was calculated as about 9.2 for Campy-Cefex and about 12.8 for the Campy-TTC agar (See Table 2 below). Campylobacter colonies grown on the Campy-TTC agar were deep red to magenta in color to the otherwise translucent Campylobacter colonies making observation easier. Significantly, no contaminating colonies were ever observed on the Campy-TTC agar plates; whereas, all of the Campy-Cefex plates supported the growth of about 13.6 non-Campylobacter cfu/plate on average.

TABLE 2

Comparison of plating media for recovery of Campylobacter from freshly processed broiler carcasses (n = 20).

| | Campy-Cefex agar | Campy-TTC agar |
|---|---|---|
| Campylobacter ssp. | | |
| Mean Campylobacter spp. cfu/ml | 9.2 | 12.8 |
| Range Campylobacter spp. cfu/ml | 0–28 | 1–39 |
| Campylobacter spp. standard deviation cfu/ml | 8.62 | 11.8 |
| Non-Campylobacter Contaminants | | |
| Mean contaminant cfu/ml | 13.6[a] | 0[b] |
| Range contaminant cfu/ml | 2–84 | 0 |

[a,b]Results with different superscripts are significantly different (P < 0.05)

EXAMPLE 3

In this example, Campylobacter recovery from freshly processed (post-chill, post-drip) broiler carcasses was compared using 3 different agar formulas; Campy-cefex, blood-containing Campy-TTC, and blood-free Campy-TTC. Buffered peptone water (BPW) for rinsing and dilution blanks were prepared and kept cold at about 4° C. Agar plates were made as described in Example 1 approximately 72 hours prior to use and allowed to sit in the dark at room temperature. Freshly processed broiler carcasses (25, post-chill, post-drip) were treated as described above in example 2. An additional 16 poultry rinses from commercial sources were obtained for testing.

A 48 hour *Campylobacter jejuni* culture was grown on Campy-cefex agar under microaerobic conditions. A spectrophotometric method was used to prepare a solution containing about $Log_{10}$ 8 cfu *C. jejuni*/ml in BPW. From this stock culture appropriate dilutions were made such that each carcass rinse (1–25) was spiked with about 1000 cfu/ml. The 16 commercial poultry rinses were not spiked with Campylobacter prior to analysis.

Samples (about 0.25 ml) from each original carcass rinse was transferred to each of 4 properly dried Campy-Cefex agar plates. Additionally, duplicate plates of each agar type were inoculated with about 0.1 ml portions of the rinse sample ($10^{-1}$ dilution). The spiked samples (1–25) were diluted about 1:10 in sterile BPW and duplicate about 0.1 ml portions were also plated on all three agar types ($10^{-2}$ dilution). All plates were incubated upside down in an incubator charged with Campy gas for about 36–48 hours at about 42° C.

Directly inoculated agar plates were removed from incubators after about 36–48 hours. Plates were inspected for growth of Campylobacter. Typical Campylobacter colonies were enumerated and confirmed using microscopic wet mount and latex agglutination, as in Example 2, for confirmation if necessary. The number of Campylobacter cfu per ml rinse was recorded for each type of agar.

Recovery of Campylobacter was recorded as cfu/ml for each sample by agar type. Statistical differences ($P<0.05$) between methods were determined by the Student-Newman-Keuls test using SigmaStat statistical software (Jandel Scientific Software, San Rafael, Calif.).

Campylobacter populations enumerated from the spiked broiler rinse samples (25) ranged from about 135–2000 cfu/ml and were most often countable on the $10^{-1}$ dilution plates. Recovery of Campylobacter was significantly greater on blood-containing Campy-TTC and blood-free Campy-TTC agars than on Campy-Cefex plates incubated under similar conditions (Table 3 below, $P<0.05$).

Campylobacter populations enumerated from the non-spiked commercial poultry rinse samples (16) ranged from 0 to about 88 cfu/ml and were most often countable by combining the counts from the 4, 0.25 ml plates to obtain a total count of cfu/ml. Recovery of Campylobacter was not significantly different between the three agars (Table 4 below, $P<0.05$). Contaminants were significantly reduced on the Campy-TTC agars as compared to the Campy-cefex agar.

TABLE 3

Comparison of plating media for recovery of Campylobacter from freshly processed broiler carcass rinses spiked with *C. jejuni* (n = 25)

|  | Campy-Cefex agar | Campy-TTC agar | BF-Campy-TTC agar |
|---|---|---|---|
| Campylobacter spp. | | | |
| Mean Campylobacter spp. cfu/ml | 766[a] | 973[b] | 977[b] |
| Mean $\log_{10}$ Campylobacter spp. cfu/ml | 2.85[a] | 2.96[b] | 2.98[b] |
| Range Campylobacter spp. cfu/ml | 368–1525 | 135–2000 | 460–1700 |
| Campylobacter spp. standard diviation cfu/ml | 320.1 | 315.2 | 246.2 |
| Non-Campylobacter Contaminants | | | |
| Mean contaminant cfu/ml | 9[a] | 0[b] | 0[b] |
| Range contaminant cfu/ml | 0–145 | 0 | 0 |

[a,b]Results with different superscripts are significantly different ($P < 0.05$)

TABLE 4

Comparison of plating media for recovery of Campylobacter from Commercial poultry rinses (n = 16).

|  | Campy-Cefex agar | Campy-TTC agar | BF-Campy-TTC agar |
|---|---|---|---|
| Campylobacter spp. | | | |
| Mean Campylobacter spp. cfu/ml | 16.8 | 16.3 | 11.4 |
| Mean $\log_{10}$ Campylobacter spp. cfu/ml | 1.22 | 1.21 | 1.06 |
| Range Campylobacter spp. cfu/ml | 0–79 | 0–88 | 0–76 |
| Campylobacter spp. standard diviation cfu/ml | 28.2 | 27.0 | 21.2 |
| Non-Campylobacter Contaminants | | | |
| Mean contaminant cfu/ml | 14.1[a] | 0[b] | 0[b] |
| Range contaminant cfu/ml | 0–72 | 0 | 0 |

[a,b]Results with different superscripts are significantly different ($P < 0.05$)

EXAMPLE 4

Recovery of Campylobacter from naturally occurring contaminated poultry carcass rinses is compared using the following media: blood-free Campy-TCC agar of Example 1, blood-free agar of Example 1 with rifampicin and amphotericin substituted for the cycloheximide, blood-free-TCC of example 1 with rifampicin and nystatin substituted for cycloheximide, and a prior art medium-Cefex. Buffered peptone water (BPW) for rinsing and dilution blanks were prepared and kept cold at about 4° C. Agar plates were made as described in Example 1 approximately 72 hours prior to use and allowed to sit in the dark at room temperature. For media containing rifampicin and amphotericin, concentrations used were about 10 mg/l for rifampicin and about 25 mg/l for amphotericin. For media containing rifampicin and nystatin, concentrations used were about 10 mg/l for rifampicin and about 50 mg/l nystatin.

Freshly processed broiler carcasses (19, post-chill, post-drip) were procured and treated as in Example 2.

Samples (approximately 0.10 ml) from each carcass rinse was transferred to duplicate plates of each agar type. All plates were incubated upside down in an incubator charged with Campy gas for about 36–48 hours at about 42° C.

The agar plates were removed from incubators after about 36–48 hours. Plates were inspected for growth of Campylobacter and enumerated as in Example 3. The number of Campylobacter cfu per ml. Rinse was recorded for each type of agar (See Table 5).

Recovery of Campylobacters on the three blood-free Campy-TCC agars was similar to recovery on Cefex agar. However, more non-campylobacter contaminants (mean of 3.3 cfu/ml) were seen on Cefex.

TABLE 5

Recovery on selected agars of Campylobacter spp. and contaminants from broiler carcass rinses

| Rinse # | Standard CLA[1] | | CLA + Rif + Amph[2] | | CLA + Rif + Nyst[3] | | Cefex[4] | |
|---|---|---|---|---|---|---|---|---|
|  | Campy cfu/ml | contam cfu/ml | Campy cfu/ml | contam cfu/ml | Campy cfu/ml | contam cfu/ml | Campy cfu/ml | contam cfu/ml |
| 1 | 31 | 0 | 23 | 0 | 15 | 0 | 39 | 5 |
| 2 | 8 | 0 | 2 | 0 | 4 | 0 | 4 | 0 |
| 3 | 15 | 0 | 14 | 0 | 12 | 0 | 21 | 5 |
| 4 | 95 | 0 | 55 | 0 | 65 | 0 | 105 | 6 |
| 5 | 298 | 0 | 196 | 0 | 138 | 0 | 330 | 1 |
| 6 | 52 | 0 | 61 | 0 | 42 | 0 | 60 | 11 |
| 7 | 29 | 0 | 22 | 0 | 16 | 0 | 32 | 1 |
| 8 | 51 | 0 | 32 | 0 | 36 | 0 | 47 | 0 |
| 9 | 18 | 0 | 17 | 0 | 10 | 0 | 22 | 2 |
| 10 | 29 | 0 | 33 | 0 | 27 | 0 | 56 | 3 |
| 11 | 60 | 0 | 61 | 0 | 44 | 0 | 104 | 2 |

TABLE 5-continued

Recovery on selected agars of Campylobacter spp. and contaminants from broiler carcass rinses

| Rinse # | Standard CLA[1] | | CLA + Rif + Amph[2] | | CLA + Rif + Nyst[3] | | Cefex[4] | |
|---|---|---|---|---|---|---|---|---|
| | Campy cfu/ml | contam cfu/ml | Campy cfu/ml | contam cfu/ml | Campy cfu/ml | contam cfu/ml | Campy cfu/ml | contam cfu/ml |
| 12 | 10 | 0 | 9 | 0 | 7 | 0 | 14 | 2 |
| 13 | 8 | 0 | 7 | 0 | 3 | 0 | 17 | 2 |
| 14 | 63 | 0 | 43 | 0 | 56 | 0 | 78 | 8 |
| 15 | 12 | 0 | 16 | 0 | 9 | 0 | 21 | 5 |
| 16 | 36 | 0 | 50 | 0 | 44 | 0 | 61 | 4 |
| 17 | 36 | 0 | 22 | 0 | 18 | 0 | 37 | 2 |
| 18 | 30 | 0 | 37 | 0 | 20 | 0 | 46 | 3 |
| 19 | 12 | 0 | 16 | 0 | 10 | 0 | 13 | 0 |
| Mean | 47.0 | 0 | 37.7 | 0 | 30.3 | 0 | 58.3 | 3.3 |

[1]Standard CLA is the original media composition containing cycloheximide and no blood;
[2]CLA (no cycloheximide) + Rifampicin (10 mg/l) + Amphotericin (25 mg/l)
[3]CLA (no cycloheximide) + Rifampicin (10 mg/l) + Nystatin (50 mg/l)
[4]Cefex is the original composition (Stern et al.)

The foregoing detailed description is for the purpose of illustration. Such detail is solely for that purpose and those skilled in the art can make variations therein without departing from the spirit and scope of the invention.

We claim:

1. A medium for recovery of Campylobacter species comprising:
    about 43 grams/liter of Brucella agar;
    about 50 milliliters/liter of lysed horse blood; or a blood-free composition containing:
        about 1.0 grams/liter α-ketoglutaric acid, about 0.6 grams/liter sodium carbonate, about 3 grams/liter yeast extract, and about 0.01 grams/liter hemin;
    about 33 milligrams/liter of cefoperizone or a cefoperizone salt;
    about 0.5 gram/liter ferrous sulfate;
    about 0.2 grams/liter of sodium bisulfite;
    about 0.5 grams/liter of pyruvic acid;
    about 10 milligrams/liter of vancomycin or a vancomycin salt;
    about 5 milligrams/liter of trimethoprim or a trimethoprim salt;
    about 0.35 milligrams/liter of polymyxin B or a polymyxin B salt;
    about 200 milligrams/liter of 2,3,5-triphenyltetrazolium chloride; and
    an antibiotic composition containing:
        (a) about 100 milligrams/liter of cycloheximide or a cycloheximide salt; or
        (b) about 10 milligrams/liter rifampicin or a rifampicin salt and about 25 milligrams/liter of amphotericin or an amphotericin salt; or
        (c) about 10 milligrams/liter of rifampicin or a rifampicin salt and about 50 milligrams/liter of nystatin or a nystatin salt.

2. A medium for recovery of Campylobacter species comprising:
    about 40–50 grams/liter Brucella Agar;
    about 20–100 milliliters/liter lysed horse blood or a blood-free composition containing:
        about 0.5–2.5 grams/liter α-ketoglutaric acid, about 0.4–0.8 grams/liter sodium carbonate, about 2–5 grams/liter yeast extract, and about 5–25 milligrams/liter hemin;
    about 20–50 milligrams/liter cefoperizine or a cefoperizine salt;
    about 0.1–1.0 grams/liter ferrous sulfate;
    about 0.05–5 grams/liter sodium bisulfate;
    about 0.1–1.0 grams/liter pyruvic acid;
    about 5–20 milligrams/liter vancomycin or a vacomycin salt;
    about 2.5–10 milligrams/liter trimethoprim or a trimethoprim salt;
    about 0.3–0.75 milligrams/liter polymyxin B or a polymyxin B salt;
    about 100–200 milligrams/liter 2,3,5-triphenyltetrazolium chloride; and
    an antibiotic composition containing:
        (a) about 100–400 milligrams/liter cycloheximide or a cycloheximide salt, or
        (b) about 5–20 milligrams/liter rifampicin or a rifampicin salt and about 10–40 milligrams/liter amphotericin or an amphotericin salt; or
        (c) about 5–20 milligrams/liter rifampicin or a rifampicin salt and about 20–80 milligrams/liter nystatin or a nystatin salt.

3. A medium for recovery of Campylobacter species comprising:
    about 43 grams/liter of Brucella agar,
    about 50 milliliters/liter of lysed horse blood,
    about 33 milligrams/liter of cefoperizone or a cefoperizone salt,
    about 0.5 gram/liter ferrous sulfate,
    about 0.2 grams/liter of sodium bisulfite,
    about 0.5 grams/liter of pyruvic acid,
    about 10 milligrams/liter of vancomycin or a vancomycin salt,
    about 5 milligrams/liter of trimethoprim or a trimethoprim salt,
    about 0.35 milligrams/liter of polymyxin B or a polymyxin B salt,
    about 200 milligrams/liter of 2,3,5-triphenyltetrazolium chloride, and
    about 100 milligrams/liter of cycloheximide or a cycloheximide salt.

4. A medium for recovery of Campylobacter species comprising:

about 43 grams/liter of Brucella agar,
about 1.0 grams/liter α-ketoglutaric acid,
about 0.6 grams/liter sodium carbonate,
about 3 grams/liter yeast extract,
about 0.01 grams/liter hemin,
about 33 milligrams/liter of cefoperizone or a cefoperizone salt,
about 0.5 gram/liter ferrous sulfate,
about 0.2 grams/liter of sodium bisulfite,
about 0.5 grams/liter of pyruvic acid,
about 10 milligrams/liter of vancomycin or a vancomycin salt,
about 5 milligrams/liter of trimethoprim or a trimethoprim salt,
about 0.35 milligrams/liter of polymyxin B or a polymyxin B salt,
about 200 milligrams/liter of 2,3,5-triphenyltetrazolium chloride, and
about 100 milligrams/liter of cycloheximide or a cycloheximide salt.

5. A medium for recovery of Campylobacter species comprising:
about 43 grams/liter of Brucella agar,
about 1.0 grams/liter α-ketoglutaric acid,
about 0.6 grams/liter sodium carbonate,
about 3 grams/liter yeast extract,
about 0.01 grams/liter hemin,
about 33 milligrams/liter of cefoperizone or a cefoperizone salt,
about 0.5 gram/liter ferrous sulfate,
about 0.2 grams/liter of sodium bisulfite,
about 0.5 grams/liter of pyruvic acid,
about 10 milligrams/liter of vancomycin or a vancomycin salt,
about 5 milligrams/liter of trimethoprim or a trimethoprim salt,
about 0.35 milligrams/liter of polymyxin B or a polymyxin B salt,
about 200 milligrams/liter of 2,3,5-triphenyltetrazolium chloride,
about 10 milligrams/liter rifampicin or a rifampicin salt, and
about 25 milligrams/liter amphotericin or an amphotericin salt.

6. A medium for recovery of Campylobacter species comprising:
about 43 grams/liter of Brucella agar,
about 1.0 grams/liter α-ketoglutaric acid,
about 0.6 grams/liter sodium carbonate,
about 3 grams/liter yeast extract,
about 0.01 grams/liter hemin,
about 33 milligrams/liter of cefoperizone or a cefoperizone salt,
about 0.5 gram/liter ferrous sulfate,
about 0.2 grams/liter of sodium bisulfite,
about 0.5 grams/liter of pyruvic acid,
about 10 milligrams/liter of vancomycin or a vancomycin salt,
about 5 milligrams/liter of trimethoprim or a trimethoprim salt,
about 0.35 milligrams/liter of polymyxin B or a polymyxin B salt,
about 200 milligrams/liter of 2,3,5-triphenyltetrazolium chloride,
about 10 milligrams/liter rifampicin, and
about 50 milligrams/liter nystatin.

7. A medium for recovery of Campylobacter species comprising:
about 40–50 grams/liter Brucella Agar,
about 20–100 milliliters/liter lysed horse blood,
about 20–50 milligrams/liter cefoperizine or a cefoperizine salt,
about 0.1–1.0 grams/liter ferrous sulfate,
about 0.05–5 grams/liter sodium bisulfate,
about 0.1–1.0 grams/liter pyruvic acid,
about 5–20 milligrams/liter vancomycin or a vacomycin salt,
about 2.5–10 milligrams/liter trimethoprim or a trimethoprim salt,
about 0.3–0.75 milligrams/liter polymyxin B or a polymyxin B salt,
about 100–200 milligrams/liter 2,3,5-triphenyltetrazolium chloride, and
about 100–400 milligrams/liter cycloheximide or a cycloheximide salt.

8. A medium for recovery of Campylobacter species comprising:
about 40–50 grams/liter Brucella Agar,
about 0.5–2.5 grams/liter α-ketoglutaric acid,
about 0.4–0.8 grams/liter sodium carbonate,
about 2–5 grams/liter yeast extract,
about 5–25 milligrams/liter hemin,
about 20–50 milligrams/liter cefoperizine or a cefoperizine salt,
about 0.1–1.0 grams/liter ferrous sulfate,
about 0.05–5 grams/liter sodium bisulfate,
about 0.1–1.0 grams/liter pyruvic acid,
about 5–20 milligrams/liter vancomycin or a vacomycin salt,
about 2.5–10 milligrams/liter trimethoprim or a trimethoprim salt,
about 0.3–0.75 milligrams/liter polymyxin B or a polymyxin B salt,
about 100–200 milligrams/liter 2,3,5-triphenyltetrazolium chloride,
about 5–20 milligrams/liter rifampicin or a rifampicin salt, and
about 10–40 milligrams/liter amphotericin or an amphotericin salt.

9. A medium for recovery of Campylobacter species comprising:
about 40–50 grams/liter Brucella Agar,
about 0.5–2.5 grams/liter α-ketoglutaric acid,
about 0.4–0.8 grams/liter sodium carbonate,
about 2–5 grams/liter yeast extract,
about 5–25 milligrams/liter hemin,
about 20–50 milligrams/liter cefoperizine or a cefoperizine salt,
about 0.1–1.0 grams/liter ferrous sulfate,
about 0.05–5 grams/liter sodium bisulfate, about 0.1–1.0 grams/liter pyruvic acid, about 5–20 milligrams/liter vancomycin or a vacomycin salt, about 2.5–10 milligrams/liter trimethoprim or a trimethoprim salt, about 0.3–0.75 milligrams/liter polymyxin B or a polymyxin B salt, about 100–200 milligrams/liter 2,3,5-triphenyltetrazolium chloride, about 5–20 milligrams/liter rifampicin or a rifampicin salt, and about 20–80 milligrams/liter nystatin or a nystatin salt.

* * * * *